(12) United States Patent
Nojiri et al.

(10) Patent No.: US 9,464,306 B2
(45) Date of Patent: Oct. 11, 2016

(54) METHOD FOR PRODUCING L-AMINO ACID

(75) Inventors: Masutoshi Nojiri, Hyogo (JP); Tozo Nishiyama, Hyogo (JP); Naoaki Taoka, Hyogo (JP)

(73) Assignee: KANEKA CORPORATION, Osaka-shi, Osaka (JP)

( * ) Notice: Subject to any disclaimer, the term of this patent is extended or adjusted under 35 U.S.C. 154(b) by 279 days.

(21) Appl. No.: 13/126,534

(22) PCT Filed: Oct. 28, 2009

(86) PCT No.: PCT/JP2009/068515
§ 371 (c)(1),
(2), (4) Date: Jun. 6, 2011

(87) PCT Pub. No.: WO2010/050516
PCT Pub. Date: May 6, 2010

(65) Prior Publication Data
US 2011/0229940 A1  Sep. 22, 2011

(30) Foreign Application Priority Data
Oct. 29, 2008  (JP) .................. 2008-277674

(51) Int. Cl.
| C12P 13/04 | (2006.01) |
| C12P 13/00 | (2006.01) |
| C12N 9/10  | (2006.01) |
| C12N 9/90  | (2006.01) |
| C07C 227/30 | (2006.01) |
| C07C 233/47 | (2006.01) |
| C12P 13/22 | (2006.01) |
| C12P 41/00 | (2006.01) |

(52) U.S. Cl.
CPC ............ *C12P 13/04* (2013.01); *C07C 227/30* (2013.01); *C07C 233/47* (2013.01); *C12N 9/104* (2013.01); *C12N 9/90* (2013.01); *C12P 13/222* (2013.01); *C12P 41/007* (2013.01); *Y02P 20/52* (2015.11)

(58) Field of Classification Search
CPC ........ C12P 13/04; C12P 41/007; C12N 9/90; C12N 9/104; C12Y 203/02
USPC ........................................ 435/106, 193, 233
See application file for complete search history.

(56) References Cited

U.S. PATENT DOCUMENTS

| 2010/0062493 A1 | 3/2010 | Araki et al. |
| 2011/0244530 A1 | 10/2011 | Toda et al. |

FOREIGN PATENT DOCUMENTS

| FR | 2566410 | 12/1985 |
| JP | 62288 | 1/1987 |
| JP | 3-94670 | 4/1991 |
| JP | 05-085999 | 4/1993 |
| JP | 05-092944 | 4/1993 |
| JP | 2000-270887 | 10/2000 |
| JP | 2001-046088 | 2/2001 |
| JP | 2001-314191 | 11/2001 |
| JP | 2001-333769 | 12/2001 |
| JP | 2002-238581 | 8/2002 |
| JP | 2006-254789 | 9/2006 |
| JP | 2007-082534 | 4/2007 |
| JP | 2008-061642 | 3/2008 |
| JP | 2008-255120 | 10/2008 |
| JP | 2008-307006 | 12/2008 |
| JP | 5744521 | 7/2015 |
| WO | 2008/102572 | 8/2008 |
| WO | 2009136500 | 11/2009 |

OTHER PUBLICATIONS

Witkowski et al. Biochemistry. Sep. 7, 1999; 38(36): 11643-50.*
International Preliminary Report on Patentability for International Application No. PCT/JP2009/068515 Issued on Jun. 7, 2011.
International Search Report for International Application No. PCT/JP2009/068515 mailed on Dec. 15, 2009.
Ringia, Erika A., et al., "Evolution of Enzymatic Activity in the Enolase Superfamily: Functional Studies of the Promiscuous o-Succinylbenzoate Synthase from Amycolatopsis", Biochemistry, 2004, 43, pp. 224-229.
Sakai, A., et al., "Evolution of Enzymatic Activity in the Enolase Superfamily: N-Succinylamino Acid Racemase and a New Pathway for the Irreversible Conversion of D- to L-Amino Acids", Biochemistry, 2006, 45, pp. 4455-4462.
Takami et al, Thermoadaptation Trait Revealed by the Genome Sequence of Thermophilic Geobacillus Kaustophilus, Nucleic Acids Re; 32(21):6292-6303.
Hayashida et al, Crystal Structure on N-acylamino Acid Racemase from Thermus Thermophilus HB8, 2008, Proteins, vol. 71, Issue 1, pp. 519-523.

* cited by examiner

Primary Examiner — Robert Mondesi
Assistant Examiner — Md. Younus Meah
(74) Attorney, Agent, or Firm — Amin, Turocy & Watson LLP

(57) ABSTRACT

The present invention relates to a method for producing an L-amino acid by reacting an enantiomeric mixture of an N-succinyl amino acid with L-succinylase in the presence of N-acylamino acid racemase to specifically hydrolyze the L-form. In particular, the present invention relates to a method for producing an L-amino acid in high yield by using an N-succinyl amino acid whose dissolved concentration is particularly low as a raw material to perform a reaction while precipitating the produced L-amino acid out of the reaction system. The present invention enables efficient production of an L-amino acid having high optical purity, particularly an L-amino acid useful as a raw material for products such as pharmaceutical products and agricultural chemicals.

8 Claims, No Drawings

METHOD FOR PRODUCING L-AMINO ACID

TECHNICAL FIELD

The present invention relates to a method for efficiently producing an L-amino acid from an enantiomeric mixture of an N-succinyl amino acid by combining the following reactions: 1) a reaction of racemizing an N-succinyl amino acid with use of N-acylamino acid racemase; and 2) a reaction of specifically hydrolyzing an N-succinyl-L-amino acid with use of L-succinylase.

BACKGROUND ART

Optically active amino acids, particularly optically active unnatural amino acids, are compounds useful as synthetic raw materials or intermediates for products such as agricultural chemicals and pharmaceutical products. Hence, how to efficiently produce an optically active amino acid, particularly an unnatural one, has been an industrially important problem.

Patent Document 1 discloses one method of solving this problem which involves optically resolving a racemic N-acetylamino acid as a raw material with D-aminoacylase or L-aminoacylase to give the D-form or L-form, whereby an amino acid having high optical purity is produced. With this method, however, the yield of an optically active amino acid is 50% at the highest, which means that half of a racemate goes to waste. Then, as disclosed in Patent Documents 2, 3, 4, and 5, N-acylamino acid racemase for racemizing the residual N-acetylamino acid has been proposed for use in combination with the aminoacylase in order to improve the yield. However, the resolution with use of a combination of N-acylamino acid racemase and aminoacylase has a low reactivity with an amino acid yield of only 70 to 75%. Further, the N-acyl substrate remains and thus a process for removing it is required. These problems have been impediments to practical applications.

Also, as described in Non-Patent Documents 1 and 2 and Patent Document 6, N-acylamino acid racemase has been found to have low reactivity to N-acylamino acids. In recent years, reports have been made as described in Non-Patent Documents 1 and 2 and Patent Document 6 that N-acylamino acid racemase has a higher reactivity to N-succinyl amino acids than to N-acetylamino acids, and that L-succinylase acts on N-succinyl forms of natural L-amino acids. Still, no method is known which efficiently produces an L-amino acid from an enantiomeric mixture of an N-succinyl amino acid with use of a combination of N-acylamino acid racemase and L-succinylase.

Also, an N-succinyl amino acid represented by the following formula (III) and a salt thereof, which are raw materials applicable to the present production method, have not been known:

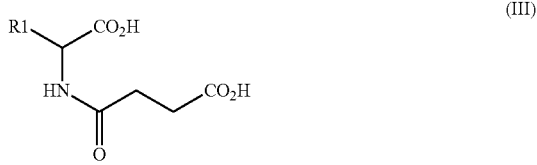

wherein R1 represents an optionally substituted C5 to C20 alkyl group, an optionally substituted C5 to C20 alkenyl group, an optionally substituted C2 to C20 alkynyl group, an optionally substituted indanyl group, an optionally substituted naphthylmethyl group, a fluorobenzyl group, a chlorobenzyl group, or a bromobenzyl group.

Patent Document 1: JP 2006-254789 A
Patent Document 2: JP 2001-46088 A
Patent Document 3: JP 2001-314191 A
Patent Document 4: JP 2002-238581 A
Patent Document 5: JP 2007-82534 A
Patent Document 6: JP 2008-61642 A
Non-Patent Document 1: Biochemistry, 2004, Vol. 43, p. 224
Non-Patent Document 2: Biochemistry, 2006, Vol. 45, p. 4455

SUMMARY OF THE INVENTION

The present invention aims to provide a more efficient method for producing an L-amino acid than the conventional methods.

As a result of eager examination to solve the above problems, the present inventors have found that the reactivity can be improved by precipitating the resulting amino acid out of the reaction system during the course of the combined reactions of racemizing an N-succinyl amino acid with N-acylamino acid racemase and specifically hydrolyzing the N-succinyl-L-amino acid with L-succinylase. Thereby, the present invention has been completed.

That is, one aspect of the present invention is a method for producing an L-amino acid by reacting an enantiomeric mixture of an N-succinyl amino acid with L-succinylase, the reaction being performed in the presence of N-acylamino acid racemase and with precipitating the produced L-amino acid.

In the production method according to the present invention, the L-amino acid preferably has a dissolved concentration of 1% by weight or lower.

In the production method according to the present invention, preferably, the N-succinyl amino acid serving as a substrate is represented by formula (I):

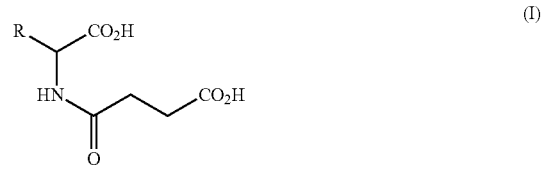

wherein R represents an optionally substituted C1 to C20 alkyl group, an optionally substituted C2 to C20 alkenyl group, an optionally substituted C2 to C20 alkynyl group, an optionally substituted C4 to C20 aryl group, or an optionally substituted C5 to C20 aralkyl group; and the L-amino acid to be produced is represented by formula (II):

wherein R is the same as defined above.
In a more preferable embodiment of the present invention, R in formula (I) and formula (II) is a 4-bromobenzyl group, a 3-fluorobenzyl group, a naphthylmethyl group, an indanyl group, or a 6-heptenyl group.

In a preferable embodiment of the present invention, a transformant transformed with a vector that contains DNA encoding the N-acylamino acid racemase and DNA encoding the L-succinylase is used as a source of the N-acylamino acid racemase and the L-succinylase.

Another aspect of the present invention is an N-succinyl amino acid represented by formula (III) or a salt thereof:

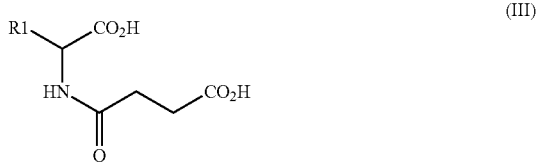

(III)

wherein R1 represents an optionally substituted C5 to C20 alkyl group, an optionally substituted C5 to C20 alkenyl group, an optionally substituted C2 to C20 alkynyl group, an optionally substituted indanyl group, an optionally substituted naphthylmethyl group, a fluorobenzyl group, a chlorobenzyl group, or a bromobenzyl group.

In a preferable embodiment of the present invention, R in formula (III) is a 4-bromobenzyl group, a 3-fluorobenzyl group, a 2-naphthylmethyl group, a 2-indanyl group, or a 6-heptenyl group.

According to the present invention, it is possible to precipitate the resulting L-amino acid out of the reaction system by using an N-succinyl amino acid whose dissolved concentration is low as a raw material for reaction. Therefore, the present invention has been found to avoid the reaction inhibition and thus enable efficient production of an L-amino acid.

BEST MODE FOR CARRYING OUT THE INVENTION

Hereinafter, the present invention is described in detail based on non-limiting embodiments.

The "enantiomeric mixture" herein refers to a mixture of the L-form and the D-form, with an amount of the D-form in the range of from more than 0% to less than 100%. An N-succinyl amino acid, a raw material used in the present invention, is represented by the following formula (I) and can be synthesized by various known methods.

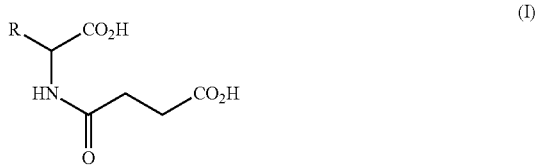

(I)

The amino acid may be produced by, for example, 1) a method of reacting, in acetic acid, an amino acid with succinic anhydride in an amount equivalent to or greater than that of the amino acid, distilling off the solvent, and recrystallizing the resulting product in ethyl acetate and/or methanol; or 2) a method of reacting an amino acid with succinic anhydride in an amount equivalent to or greater than that of the amino acid, in water while maintaining an alkaline pH, and then adjusting the pH to acidic to crystallize the resulting product.

R in the formula (I) represents an optionally substituted C1 to C20 alkyl group, an optionally substituted C2 to C20 alkenyl group, an optionally substituted C4 to C20 aryl group, or an optionally substituted C5 to C20 aralkyl group.

The C1 to C20 alkyl group may be a straight chain or branched chain, and examples thereof include methyl, ethyl, n-propyl, isopropyl, n-butyl, sec-butyl, tert-butyl, pentanyl, hexanyl, heptanyl, and octanyl. Examples of the C2 to C20 alkenyl group include ethenyl, propenyl, butenyl, pentenyl, hexenyl, heptenyl, and octenyl.

Examples of the C2 to C20 alkynyl group include ethynyl, propynyl, butynyl, pentynyl, hexynyl, heptynyl, and octynyl.

Examples of the C4 to C20 aryl group include phenyl, naphthyl, anthranyl, pyridyl, pyrimidyl, indanyl, and indenyl.

Examples of the C5 to C20 aralkyl group include benzyl, naphthylmethyl, anthranylmethyl, pyridylmethyl, pyrimidylmethyl, indanylmethyl, and indanylmethyl.

Each of the alkyl group, alkenyl group, alkynyl group, aryl group, and aralkyl group may optionally be substituted. Examples of the substituent include a halogen atom, hydroxyl, amino, and nitro.

Specific examples of the N-succinyl amino acid represented by formula (I) include N-succinyl-DL-4-bromophenylalanine, N-succinyl-DL-3-fluorophenylalanine, N-succinyl-DL-2-naphthylalanine, N-succinyl-DL-2-indanylglycine, and N-succinyl-DL-6-heptenylglycine.

The L-succinylase used in the present invention is an enzyme that hydrolyzes (desuccinylates) the succinyl group of an N-succinyl amino acid represented by formula (I) in an L-form selective manner. The N-acylamino acid racemase used in the present invention is an enzyme that racemizes the enantiomers of an N-succinyl amino acid represented by formula (I).

In the reaction of the present invention, only the L-form in an enantiomeric mixture of an N-succinyl amino acid is specifically hydrolyzed (desuccinylated) by L-succinylase, and thereby the desired L-amino acid is produced. As a result, the N-succinyl-D-amino acid becomes excess, and then N-acylamino acid racemase racemizes the N-succinyl-D-amino acid to the N-succinyl-DL-amino acid. The N-succinyl-L-amino acid produced by N-acylamino acid racemase is converted into the desired L-amino acid by L-succinylase.

As above, the combination of the reaction of specifically hydrolyzing the L-form and the racemization reaction enables conversion of an enantiomeric mixture of an N-succinyl amino acid to an L-amino acid comprising substantially a single enantiomer. In a more preferable embodiment of the present invention, the L-amino acid is precipitated out of the reaction system when the concentration of the L-amino acid accumulated reaches and exceeds the dissolved concentration thereof during the course of the reaction or after completion of the reaction. Thus, the reaction efficiently proceeds.

It should be noted that an enantiomeric mixture of an N-succinyl amino acid can be efficiently converted to a D-amino acid comprising substantially a single enantiomer when highly active D-succinylase (which performs D-form selective desuccinylation) is used according to the principle of the present invention. As an enzyme for hydrolyzing an N-succinyl amino acid in a D-form selective manner, D-aminoacylase is known as described in JP 2008-61642 A, but D-aminoacylase has not been demonstrated to have practical activity.

Here, the "dissolved concentration" refers to percentage (%) by weight of an amino acid dissolvable in the reaction mixture after completion of the reaction, and can be measured by the following method. That is, the L-amino acid is added to the reaction mixture after completion of the reaction until the L-amino acid is no longer dissolved. After that, the mixture is centrifuged, and the resulting supernatant is filtered. The amino acid present in the filtrate is quantitatively analyzed by high performance liquid chromatography, and the percentage (%) by weight of the amino acid is calculated.

On the other hand, the percentage (%) by weight of the produced amino acid (including the precipitated amino acid and the dissolved amino acid) in the reaction mixture after completion of the reaction can be measured by the following method. That is, the reaction mixture, including the precipitated amino acid, after completion of the reaction is uniformly sampled. Then, the precipitated amino acid is solubilized with an appropriate solvent, the amino acid in the resulting solution is quantitatively analyzed by high performance liquid chromatography, and the percentage (%) by weight of the amino acid is calculated.

The dissolved concentration is preferably 3% by weight or lower, and more preferably 1% by weight or lower. Since the L-amino acid is precipitated when the amount of the produced L-amino acid exceeds the dissolved concentration, a higher percentage (%) by weight of the produced amino acid in the reaction mixture after completion of the reaction is more suitable. The percentage (%) by weight of the produced amino acid is preferably twice or more the dissolved concentration, and more preferably five times or more the dissolved concentration.

The method for producing an L-amino acid according to the present invention can be performed by putting, in an appropriate solvent, an enantiomeric mixture of an N-succinyl amino acid serving as a substrate, together with L-succinylase and N-acylamino acid racemase.

The solvent for the reaction may be an aqueous solvent, or may be a mixture of an aqueous solvent and an organic solvent. Examples of the organic solvent include toluene, ethyl acetate, n-butyl acetate, hexane, isopropanol, diisopropyl ether, methanol, acetone, and dimethyl sulfoxide. The reaction is carried out at a temperature of, for example, 10° C. to 70° C., and preferably of 30° C. to 55° C. The pH of the reaction mixture is maintained at, for example, 4 to 10, and preferably at 6 to 9.

The reaction can be carried out by a batch method or a continuous method. In the case of a batch method, the initial concentration of the reaction substrate is, for example, 0.1% to 70% (w/v), and preferably 3% to 50% (w/v).

Each of L-amino acids that can be produced by the reaction may be isolated and purified by a known method. For example, the L-amino acid may be isolated and purified by performing a treatment such as chromatography on the reaction mixture containing the produced L-amino acid, or alternatively by removing microbial cells from the reaction mixture through filtration, neutralizing the filtrate with, for example, hydrochloric acid for crystallization, and filtering the precipitated desired compound. The filtrate obtained by removing microbial cells from the reaction mixture may be used directly for the subsequent reaction in the next process.

The N-Acylamino acid racemase used in the present invention has ability to racemize N-succinyl amino acids represented by the above formula (I). Such an enzyme to be used is not particularly limited, and specific examples thereof include enzymes derived from microorganisms of the genera *Geobacillus* and *Thermus*. The enzyme is preferably one derived from a microorganism such as *Geobacillus kaustophilus* or *Thermus thermophilus*, and more preferably one derived from *Geobacillus kaustophilus* NBRC 102445 or *Thermus thermophilus* HB8. The gene encoding the amino acid sequence of the N-acylamino acid racemase derived from *Geobacillus kaustophilus* NBRC 102445 is shown by SEQ ID No. 2.

The L-succinylase used in the present invention has ability to hydrolyze the L-form of N-succinyl amino acids represented by formula (I). Such an enzyme to be used is not particularly limited, and typical examples thereof include enzymes derived from microorganisms of the genus *Geobacillus*. The enzyme is preferably one derived from a microorganism such as *Geobacillus kaustophilus*. The enzyme is more preferably one derived from *Geobacillus kaustophilus* NBRC 102445, and the gene encoding its amino acid sequence is shown by SEQ ID No. 1.

These microorganisms are available from various depositories to persons skilled in the art. Examples of the depositories include those which correspond to the accession numbers referring to the microorganisms. Specifically, the microorganisms referred by the NBRC numbers are available from NITE Biological Resource Center, National Institute of Technology and Evaluation located at 2-5-8 Kazusakamatari, Kisarazu-shi, Chiba, Japan. The microorganisms can alternatively be isolated from nature sources. Here, the microorganisms can be mutated to generate strains having properties that are more advantageous in the present reaction. Also, enzyme genes isolated from the microorganisms can be introduced into various host-vector systems by a common method, and the resulting transformants can be used in the present invention.

In the present invention, a liquid microbial culture obtained by culturing such a microorganism or transformant in an appropriate culture medium, or a treated product of the culture may be used as a source of the enzyme. Examples of the treated product include culture supernatants obtained by harvesting cells from a liquid microbial culture by a method such as centrifugation, microbial cells, disrupted microbial cells, cell-free extracts obtained from the disrupted cells, immobilized cells, purified enzymes, and immobilized enzymes.

The gene manipulation, such as DNA isolation, vector preparation, and transformation, described herein can be performed, unless otherwise noted, by a method described in literature such as Molecular Cloning 2nd Edition (Cold Spring Harbor Laboratory Press, 1989) and Current Protocols in Molecular Biology (Greene Publishing Associates and Wiley-Interscience).

Examples of the "host" described herein include bacteria, yeast, filamentous fungi, plant cells, and animal cells. Among these, bacteria are preferable, and *Escherichia coli* is particularly preferable in terms of the efficiency of introduction and expression. A vector containing DNA can be introduced into a host cell by a known method. In the case of using *Escherichia coli* as the host cell, for example, the vector can be introduced into the host of commercially available *Escherichia coli* HB101 Competent Cells (produced by Takara Bio Inc.).

The "vector" described herein is not particularly limited as long as it can express a gene encoded by DNA in an appropriate host. Examples of such a vector include plasmid vectors, phage vectors, and cosmid vectors. Also, shuttle vectors may be used which enable genetic exchange between different host strains.

Such a vector usually contains a regulatory factor such as a lacUV5 promoter, a trp promoter, a trc promoter, a tac promoter, an lpp promoter, a tufB promoter, a recA promoter, or a pL promoter, and can be suitably used as an expression vector containing an expression unit in which the regulatory factor is operably linked to DNA. For example, pUCN18 can be suitably used. The plasmid pUCN18 is a plasmid obtained by substituting the 185th base T of pUC18 (produced by Takara Bio Inc., GenBank Accession No. L09136) by A through PCR for destruction of the NdeI site, and then further substituting the 471-472nd bases GC by TG for introduction of a new NdeI site.

The regulatory factor refers to a base sequence that includes a functional promoter and an arbitrary related transcription element(s) (e.g., enhancer, CCAAT box, TATA box, SPI site). The phrase "operably linked" means that various regulatory elements for regulating gene expression, such as a promoter and an enhancer, are linked to a gene in such a manner that they can operate in host cells. It is well known to those skilled in the art that the type and kind of the regulatory factor may vary depending on the host.

The "transformant" described herein can be prepared by incorporating DNA encoding a polypeptide into a vector, and then introducing the vector into a host cell. The "transformant" described herein encompasses not only microbial cultures but treated products thereof. Examples of the treated products include cells treated with a surfactant or an organic solvent, dried cells, disrupted cells, crude cell extracts, and their immobilized products prepared by known methods. The transformant described herein can be cultured in an ordinary liquid nutrient medium containing components such as a carbon source, a nitrogen source, inorganic salts, and organic nutrients, as long as the transformant grows in the medium.

At the time of carrying out the production method of the present invention, a transformant may be used which has both DNA encoding N-acylamino acid racemase and DNA encoding L-succinylase introduced therein and thus has activities of both N-acylamino acid racemase and L-succinylase. Use of such a transformant eliminates the need for separate preparation of N-acylamino acid racemase and L-succinylase, and thereby makes it easier to carry out the production method of the present invention.

The transformant containing both DNA encoding N-acylamino acid racemase and DNA encoding L-succinylase according to the present invention can be prepared by incorporating both DNA encoding N-acylamino acid racemase and DNA encoding L-succinylase into one and the same vector and then introducing the vector into a host cell, or by incorporating the two pieces of DNA into two vectors of different incompatibility groups, respectively, and then introducing the two vectors into one and the same host cell. Examples of the transformant containing both DNA encoding N-acylamino acid racemase and DNA encoding L-succinylase according to the present invention include later-described *E. coli* HB101 (pNIGHK).

EXAMPLES

Hereinafter, the present invention will be described in detail based on Examples which, however, are not intended to limit the scope of the present invention. In the following, "%" refers to "% by weight" unless otherwise noted.

Reference Example 1

Preparation of L-Succinylase

PCR was carried out with use of a DNA polymerase PrimeSTAR (produced by Takara Shuzo Co., Ltd.) to prepare a gene in which an EcoRI recognition site and a BamHI recognition site are added to an L-succinylase gene (SEQ ID No. 1) derived from *Geobacillus kaustophilus* NBRC 102445. This DNA fragment prepared by PCR was inserted into the plasmid pUCN18 (a plasmid obtained by substituting the 185th base T of pUC18 (produced by Takara Bio Inc., GenBank Accession No. L09136) by A through PCR for destruction of the NdeI site, and then further substituting the 471-472nd bases GC by TG for introduction of a new NdeI site) at between the EcoRI recognition site and the BamHI recognition site downstream from the lac promoter, whereby a recombinant vector pNHK was constructed. With use of the recombinant vector pNHK, *E. coli* HB101 Competent Cells (produced by Takara Bio Inc.) were transformed to provide *E. coli* HB101 (pNHK). The obtained transformant was inoculated into 5 ml of a 2xYT medium (1.6% tryptone, 1.0% yeast extract, 0.5% NaCl, pH 7.0) containing 200 µg/ml of ampicillin and shake-cultured at 37° C. for 24 hours. Cells were collected from the culture by centrifugation and then suspended in 5 ml of a 100 mM phosphate buffer (pH 7.0). The cells in the suspension were disrupted using a model UH-50 ultrasonic homogenizer (produced by SMT Co., Ltd.) and cell debris was then removed by centrifugation to provide a cell-free extract. The cell-free extract was assayed for the succinylase activity, and the assayed succinylase activity was 5 U.

Reference Example 2

L-Succinylase Activity Assay

The succinylase activity of L-succinylase was assayed by the following method. First, 250 µl of a substrate N-succinyl-DL-phenylalanine solution (final concentration: 50 mM) and 230 µl of Tris-HCl (0.5 M/pH 7.5) were mixed. To this mixture, 20 µl of an enzyme liquid was added, and the reaction was allowed to proceed at 30° C. After an appropriate period of time, the reaction was terminated by addition of 1 N HCl. The produced L-phenylalanine was quantified by high performance liquid chromatography, and the enzyme activity was calculated. One unit (U) of the enzyme activity was defined as 1 µmole of L-phenylalanine produced per minute from N-succinyl-DL-phenylalanine.

Reference Example 3

Preparation of N-Acylamino Acid Racemase

PCR was carried out with use of a DNA polymerase PrimeSTAR (produced by Takara Shuzo Co., Ltd.) to prepare a gene in which an EcoRI recognition site and a SadI recognition site are added to an N-acylamino acid racemase gene (SEQ ID No. 2) derived from *Geobacillus kaustophilus* NBRC 102445. This DNA fragment prepared by PCR was inserted into the plasmid pUCN18 at between the EcoRI recognition site and the SadI recognition site downstream from the lac promoter, whereby a recombinant vector pNIG was constructed. With use of the recombinant vector pNIG, *E. coli* HB101 Competent Cells (produced by Takara Bio Inc.) were transformed to provide *E. coli* HB101 (pNIG). The obtained transformant was inoculated into 5 ml of a 2xYT medium (1.6% tryptone, 1.0% yeast extract, 0.5% NaCl, pH 7.0) containing 200 μg/ml of ampicillin and shake-cultured at 37° C. for 24 hours. Cells were collected from the culture by centrifugation and then suspended in 5 ml of a 100 mM phosphate buffer (pH 7.0). The cells in the suspension were disrupted using a model UH-50 ultrasonic homogenizer (produced by SMT Co., Ltd.) and cell debris was then removed by centrifugation to provide a cell-free extract. The cell-free extract was assayed for the N-acylamino acid racemase activity, and the assayed N-acylamino acid racemase activity was 2 U. Also, PCR was carried out with use of a DNA polymerase PrimeSTAR (produced by Takara Shuzo Co., Ltd.) to prepare a gene in which an NdeI recognition site and an EcoRI recognition site are added to an N-acylamino acid racemase gene (SEQ ID No. 3) derived from *Thermo thermophilus* HB8. This DNA fragment prepared by PCR was inserted into the plasmid pUCN18 at between the NdeI recognition site and the EcoRI recognition site downstream from the lac promoter, whereby a recombinant vector pNIT was constructed. With use of the recombinant vector pNIT, *E. coli* HB101 Competent Cells (produced by Takara Bio Inc.) were transformed to provide *E. coli* HB101 (pNIT). The obtained transformant was inoculated into 5 ml of a 2xYT medium (1.6% tryptone, 1.0% yeast extract, 0.5% NaCl, pH 7.0) containing 200 μg/ml of ampicillin and shake-cultured at 37° C. for 24 hours. Cells were collected from the culture by centrifugation and then suspended in 5 ml of a 100 mM phosphate buffer (pH 7.0). The cells in the suspension were disrupted using a model UH-50 ultrasonic homogenizer (produced by SMT Co., Ltd.) and cell debris was then removed by centrifugation to provide a cell-free extract. The cell-free extract was assayed for the N-acylamino acid racemase activity, and the assayed N-acylamino acid racemase activity was 1 U.

Reference Example 4

N-Acylamino Acid Racemase Activity Assay

The racemase activity of N-acylamino acid racemase was assayed by the following method. First, 100 μl of a substrate N-acetyl-D-methionine solution (final concentration: 20 mM), 5 μl of a cobalt chloride aqueous solution (final concentration: 1 mM), 50 μl of Tris-HCl (0.5 M/pH 7.5) (final concentration: 50 mM), and 245 μl of sterile distilled water were mixed. To this mixture, 50 μl of an L-aminoacylase solution (20 mg/ml, for deacylating N-acetyl-L-methionine produced by racemase so as to produce L-methionine) and 50 μl of an enzyme liquid were added, and the reaction was allowed to proceed at 30° C. After an appropriate period of time, the reaction was terminated by addition of 1 N HCl. The produced L-methionine was quantified by high performance liquid chromatography, and the enzyme activity was calculated. One unit (U) of the enzyme activity was defined as 1 μmole of N-acetyl-L-methionine produced per minute from N-acetyl-D-methionine.

Example 1

Production of L-4-Bromophenylalanine

An amount of 2.2 g of DL-4-bromophenylalanine, 0.99 g of succinic anhydride, and 20 ml of acetic acid were mixed and reacted at 55° C. for four hours. The reaction mixture was concentrated and the residue was crystallized from ethyl acetate to give 2.1 g of N-succinyl-DL-4-bromophenylalanine. A substrate solution (pH 8) of N-succinyl-DL-4-bromophenylalanine was prepared, and a cobalt chloride aqueous solution was added thereto to give a final concentration of 1 mM. To the resulting solution, a liquid culture of *E. coli* HB101 (pNHK) and a liquid culture of *E. coli* HB101 (pNIG), which were respectively obtained by culture as in Reference Example 1 and Reference Example 3, were added (final substrate concentration: 8% by weight), and reacted at 45° C. As a result, 4-bromophenylalanine was precipitated in the reaction mixture. The reaction mixture was stirred for 18 hours, and then the substrate and the product in the reaction mixture were analyzed by high performance liquid chromatography for the conversion (mol %) and the optical purity (% e.e.). The conversion was 98.0 mol %, and the optical purity of L-4-bromophenylalanine was 100% e.e. The concentration of L-4-bromophenylalanine accumulated, which was calculated from the conversion, was 5.5% by weight. Also, the dissolved concentration of L-4-bromophenylalanine was determined by quantitative analysis using high performance liquid chromatography. The dissolved concentration was 0.5% by weight or lower.

Conversion (mol %)=amount of product/(amount of residual substrate+amount of product)×100

Optical purity (% e.e.)=(A−B)/(A+B)×100 (A is the amount of the target enantiomer, and B is the amount of the opposite enantiomer)

<High Performance Liquid Chromatography Analysis Condition>

[Analysis of Conversion]
Column: COSMOSIL 5C18-AR-II (4.6 mmϕ×250 mm, produced by Nacalai Tesque, Inc.)
Eluent: 20 mM phosphoric acid aqueous solution (pH 2.5)/acetonitrile=8/2
Flow rate: 1.0 ml/min.
Column temperature: 30° C.
Measuring wavelength: 210 nm

[Analysis of Optical Purity]
Column: CROWNPAC CR(+)(4.6 mmϕ×150 mm, produced by Daicel Chemical Industries, Ltd.)
Eluent: perchloric acid aqueous solution (pH 1.5)/methanol=85/15
Flow rate: 1.0 ml/min.
Column temperature: 30° C.
Measuring wavelength: 210 nm N-Succinyl-DL-4-bromophenylalanine $^1$H-NMR (400 MHz, CD$_3$OD) δ ppm: 2.44-2.56 (4H, m), 2.94 (1H, dd, J=8.6 Hz, J=13.9 Hz), 3.14 (1H, dd, J=5.4 Hz, J=13.9 Hz), 4.62-4.66 (1H, m), 7.14-7.19 (2H, m), 7.39-7.43 (2H, m).

Example 2

Production of L-3-fluorophenylalanine

An amount of 2.0 g of DL-3-fluorophenylalanine, 0.99 g of succinic anhydride, and 20 ml of acetic acid were mixed and reacted at 55° C. for four hours. The reaction mixture was concentrated and the residue was crystallized from ethyl acetate to give 1.9 g of N-succinyl-DL-3-fluorophenylalanine. A substrate solution (pH 8) of N-succinyl-DL-3-fluorophenylalanine was prepared, and a cobalt chloride aqueous solution was added thereto to give a final concentration of 1 mM. To the resulting solution, a liquid culture of *E. coli* HB101 (pNHK) and a liquid culture of *E. coli* HB101 (pNIG), which were respectively obtained by culture as in Reference Example 1 and Reference Example 3, were added (final substrate concentration: 8% by weight), and reacted at 45° C. As a result, 3-fluorophenylalanine was precipitated in the reaction mixture. The reaction mixture was stirred for 20 hours, and then the substrate and the product in the reaction mixture were analyzed by high performance liquid chromatography for the conversion (mol %) and the optical purity (% e.e.). The conversion was 97.5 mol %, and the optical purity of L-3-fluorophenylalanine was 100% e.e. The concentration of L-3-fluorophenylalanine accumulated, which was calculated from the conversion, was 5.1% by weight. Also, the dissolved concentration of L-3-fluorophenylalanine was determined by quantitative analysis using high performance liquid chromatography. The dissolved concentration was 0.5% by weight or lower.

Conversion (mol %)=amount of product/(amount of residual substrate+amount of product)×100

Optical purity (% e.e.)=(A−B)/(A+B)×100 (A is the amount of the target enantiomer, and B is the amount of the opposite enantiomer)
<High Performance Liquid Chromatography Analysis Condition>
[Analysis of Conversion]
Column: COSMOSIL 5C18-AR-II (4.6 mmϕ×250 mm, produced by Nacalai Tesque, Inc.)
Eluent: 20 mM phosphoric acid aqueous solution (pH 2.5)/acetonitrile=8/2
Flow rate: 1.0 ml/min.
Column temperature: 30° C.
Measuring wavelength: 210 nm
[Analysis of Optical Purity]
Column: CROWNPAC CR(+)(4.6 mmϕ×150 mm, produced by Daicel Chemical Industries, Ltd.)
Eluent: perchloric acid aqueous solution (pH 1.5)/methanol=85/15
Flow rate: 1.0 ml/min.
Column temperature: 30° C.
Measuring wavelength: 210 nm Example 3

Production of L-2-naphthylalanine

An amount of 2.0 g of DL-2-naphthylalanine, 1.02 g of succinic anhydride, and 25 ml of acetic acid were mixed and reacted at 55° C. for four hours. The reaction mixture was concentrated and the residue was crystallized from ethyl acetate to give 2.3 g of N-succinyl-DL-2-naphthylalanine. A substrate solution (pH 8) of N-succinyl-DL-2-naphthylalanine was prepared, and a cobalt chloride aqueous solution was added thereto to give a final concentration of 1 mM. To the resulting solution, a liquid culture of E. coli HB101 (pNHK) and a liquid culture of E. coli HB101 (pNIG), which were respectively obtained by culture as in Reference Example 1 and Reference Example 3, were added (final substrate concentration: 9% by weight), and reacted at 45° C. As a result, 2-naphthylalanine was precipitated in the reaction mixture. The reaction mixture was stirred for 20 hours, and then the substrate and the product in the reaction mixture were analyzed by high performance liquid chromatography for the conversion (mol %) and the optical purity (% e.e.). The conversion was 99.8 mol %, and the optical purity of L-2-naphthylalanine was 100% e.e. The concentration of L-2-naphthylalanine accumulated, which was calculated from the conversion, was 6.2% by weight. Also, the dissolved concentration of L-2-naphthylalanine was determined by quantitative analysis using high performance liquid chromatography. The dissolved concentration was 0.2% by weight or lower.

Conversion (mol %)=amount of product/(amount of residual substrate+amount of product)×100

Optical purity (% e.e.)=(A−B)/(A+B)×100 (A is the amount of the target enantiomer, and B is the amount of the opposite enantiomer)
<High Performance Liquid Chromatography Analysis Condition>
[Analysis of Conversion]
Column: COSMOSIL 5C18-AR-II (4.6 mmϕ×250 mm, produced by Nacalai Tesque, Inc.)
Eluent: 20 mM phosphoric acid aqueous solution (pH 2.5)/acetonitrile=8/2
Flow rate: 1.0 ml/min.
Column temperature: 30° C.
Measuring wavelength: 210 nm
[Analysis of Optical Purity]
Column: CHIROBIOTIC T (4.6 mmϕ×250 mm, produced by Astec)
Eluent: water/ethanol=3/7
Flow rate: 0.5 ml/min.
Column temperature: 40° C.
Measuring wavelength: 210 nm
N-Succinyl-DL-2-naphthylalanine $^1$H-NMR (400 MHz, $CD_3OD$) δ ppm: 2.38-2.50 (4H, m), 3.14 (2H, dd, J=8.5 Hz, J=13.9 Hz), 4.74-4.87 (1H, m), 7.36-7.45 (3H, m), 7.05-7.15 (4H, m).

Example 4

Production of L-2-Indanylglycine

An amount of 2.5 g of DL-2-indanylglycine, 1.44 g of succinic anhydride, and 30 ml of acetic acid were mixed and reacted at 55° C. for four hours. The reaction mixture was concentrated and the residue was crystallized from ethyl acetate to give 3.2 g of N-succinyl-DL-2-indanylglycine. A substrate solution (pH 8) of N-succinyl-DL-2-indanylglycine was prepared, and a cobalt chloride aqueous solution was added thereto to give a final concentration of 1 mM. To the resulting solution, a liquid culture of E. coli HB101 (pNHK) and a liquid culture of E. coli HB101 (pNIG), which were respectively obtained by culture as in Reference Example 1 and Reference Example 3, were added (final substrate concentration: 8% by weight), and reacted at 45° C. As a result, 2-indanylglycine was precipitated in the reaction mixture. The reaction mixture was stirred for 20 hours, and then the substrate and the product in the reaction mixture were analyzed by high performance liquid chromatography for the conversion (mol %) and the optical purity (% e.e.). The conversion was 100 mol %, and the optical purity of L-2-indanylglycine was 100% e.e. The concentration of L-2-indanylglycine accumulated, which was calculated from the conversion, was 5.3% by weight. Also, the dissolved concentration of L-2-indanylglycine was determined by quantitative analysis using high performance liquid chromatography. The dissolved concentration was 0.5% by weight or lower.

Conversion (mol %)=amount of product/(amount of residual substrate+amount of product)×100

Optical purity (% e.e.)=(A−B)/(A+B)×100 (A is the amount of the target enantiomer, and B is the amount of the opposite enantiomer)
<High Performance Liquid Chromatography Analysis Condition>
[Analysis of Conversion]
Column: COSMOSIL 5C18-AR-II (4.6 mmϕ×250 mm, produced by Nacalai Tesque, Inc.)
Eluent: 20 mM phosphoric acid aqueous solution (pH 2.5)/acetonitrile=8/2
Flow rate: 1.0 ml/min.
Column temperature: 30° C.

Measuring wavelength: 210 nm
[Analysis of Optical Purity]
Column: CROWNPAC CR(+)(4.6 mmϕ×150 mm, produced by Daicel Chemical Industries, Ltd.)
Eluent: perchloric acid aqueous solution (pH 1.5)/methanol=85/15
Flow rate: 1.0 ml/min.
Column temperature: 35° C.
Measuring wavelength: 210 nm
N-Succinyl-DL-2-indanylglycine $^1$H-NMR (400 MHz, $CD_3OD$) δ ppm: 2.47-2.61 (4H, m), 2.79-3.31 (5H, m), 4.51 (1H, d, J=6.8 Hz), 7.05-7.15 (4H, m).

Example 5

Production of L-6-heptenylglycine

An amount of 2.0 g of DL-6-heptenylglycine, 1.29 g of succinic anhydride, and 20 ml of acetic acid were mixed and reacted at 55° C. for four hours. The reaction mixture was concentrated and the residue was crystallized from ethyl acetate to give 1.4 g of N-succinyl-DL-6-heptenylglycine. A substrate solution (pH 8) of N-succinyl-DL-6-heptenylglycine was prepared, and a cobalt chloride aqueous solution was added thereto to give a final concentration of 1 mM. To the resulting solution, a liquid culture of E. coli HB101 (pNHK) and a liquid culture of E. coli HB101 (pNIG), which were respectively obtained by culture as in Reference Example 1 and Reference Example 3, were added (final substrate concentration: 9% by weight), and reacted at 45° C. As a result, 6-heptenylglycine was precipitated in the reaction mixture. The reaction mixture was stirred for 24 hours, and then the substrate and the product in the reaction mixture were analyzed by high performance liquid chromatography for the conversion (mol %). The conversion was 99.6 mol %. Then, the product was derivatized with di-tert-butyl dicarbonate to form N-tert-butoxycarbonyl-6-heptenylglycine, and the derivative was analyzed by high performance liquid chromatography for the optical purity (% e.e.). The optical purity was 100% e.e. The concentration of L-6-heptenylglycine accumulated, which was calculated from the conversion, was 5.7% by weight. Also, the dissolved concentration of L-6-heptenylglycine was determined by quantitative analysis using high performance liquid chromatography. The dissolved concentration was 0.5% by weight or lower.
<High Performance Liquid Chromatography Analysis Condition>
[Analysis of Conversion]
Column: YMC-A303 (4.6 mmϕ×250 mm, produced by YMC Co., Ltd.)
Eluent: 20 mM phosphoric acid aqueous solution (pH 2.5)/acetonitrile=1/1
Flow rate: 1.0 ml/min.
Column temperature: 35° C.
Measuring wavelength: 210 nm
[Analysis of Optical Purity]
Column: CHIRALPAK AD-RH (4.6 mmϕ×150 mm, produced by Daicel Chemical Industries, Ltd.)
Eluent: 0.02% phosphoric acid aqueous solution (pH 2.5)/acetonitrile=65/35
Flow rate: 0.7 ml/min.
Column temperature: 35° C.
Measuring wavelength: 205 nm
N-Succinyl-DL-6-heptenylglycine $^1$H-NMR (400 MHz, DMSO-$d_6$) δ ppm: 1.25-1.38 (6H, m), 1.51-1.69 (2H, m), 2.01 (2H, q, J=6.6 Hz), 2.32-2.44 (4H, m), 4.16 (1H, dt, J=5.2 Hz, J=8.6 Hz), 4.93 (1H, d, J=10.2 Hz), 4.99 (1H, d, J=17.1 Hz), 5.79 (1H, m), 8.08 (1H, d, J=7.1 Hz).

Comparative Example

Production of L-Phenylalanine

An amount of 5.0 g of DL-phenylalanine, 3.0 g of succinic anhydride, and 30 ml of acetic acid were mixed and reacted at 55° C. for four hours. The reaction mixture was concentrated and the residue was crystallized from ethyl acetate to give 4.5 g of N-succinyl-DL-phenylalanine. A substrate solution (pH 8) of N-succinyl-DL-phenylalanine was prepared, and a cobalt chloride aqueous solution was added thereto to give a final concentration of 1 mM. To the resulting solution, a liquid culture of E. coli HB101 (pNHK) and a liquid culture of E. coli HB101 (pNIG), which were respectively obtained by culture as in Reference Example 1 and Reference Example 3, were added (final substrate concentration: 6% by weight), and reacted at 45° C. The reaction mixture was stirred for 21 hours, and then the substrate and the product in the reaction mixture were analyzed by high performance liquid chromatography for the conversion (mol %) and the optical purity (% e.e.). The conversion was 86.0 mol %, and the optical purity of L-phenylalanine was 100% e.e. The concentration of L-phenylalanine accumulated, which was calculated from the conversion, was 3.2% by weight. Also, the dissolved concentration of L-phenylalanine was determined by quantitative analysis using high performance liquid chromatography. The dissolved concentration was 4% by weight.

Conversion (mol %)=amount of product/(amount of residual substrate+amount of product)×100

Optical purity (% e.e.)=(A−B)/(A+B)×100 (A is the amount of the target enantiomer, and B is the amount of the opposite enantiomer)
<High Performance Liquid Chromatography Analysis Condition>
[Analysis of Conversion]
Column: COSMOSIL 5C18-AR-II (4.6 mmϕ×250 mm, produced by Nacalai Tesque, Inc.)
Eluent: 20 mM phosphoric acid aqueous solution (pH 2.5)/acetonitrile=8/2
Flow rate: 1.0 ml/min.
Column temperature: 30° C.
Measuring wavelength: 210 nm
[Analysis of Optical Purity]
Column: CROWNPAC CR(−)(4.6 mmϕ×150 mm, produced by Daicel Chemical Industries, Ltd.)
Eluent: perchloric acid aqueous solution (pH 2.5)
Flow rate: 1.0 ml/min.
Column temperature: 35° C.
Measuring wavelength: 254 nm Example 6

Preparation of Transformant Transformed by Vector Containing L-Succinylase Gene and N-Acylamino Acid Racemase Gene PCR was carried out with use of DNA polymerase PrimeSTAR (produced by Takara Shuzo Co., Ltd.) to prepare a gene in which a SadI recognition site and a BamHI recognition site are added to an L-succinylase gene (SEQ ID No. 1) derived from Geobacillus kaustophilus NBRC 102445 and having the 615th base C substituted by G. This DNA fragment prepared by PCR was inserted into the plasmid pNIG prepared in Reference Example 3 at between the SadI recognition site and the BamHI recognition site, whereby a recombinant vector pNIGHK was constructed. With use of the recombinant vector pNIGHK, *E. coli* HB101 Competent Cells (produced by Takara Bio Inc.) were transformed to provide *E. coli* HB101 (pNIGHK). The obtained transformant was inoculated into 5 ml of a 2xYT medium (1.6% tryptone, 1.0% yeast extract, 0.5% NaCl, pH 7.0) containing 200 μg/ml of ampicillin and shake-cultured at 37° C. for 24 hours. Cells were collected from the culture by centrifugation and then suspended in 5 ml of a 100 mM phosphate buffer (pH 7.0). The cells in the suspension were disrupted using a model UH-50 ultrasonic homogenizer (produced by SMT Co., Ltd.) and cell debris was then removed by centrifugation to provide a cell-free extract. The cell-free extract was assayed for the succinylase activity and the N-acylamino acid racemase activity, and the assayed succinylase activity was 4 U and the N-acylamino acid racemase activity was 1U.

Example 7

Production of L-6-Heptenylglycine with Use of Transformant Transformed by Vector Containing L-Succinylase Gene and N-Acylamino Acid Racemase Gene A substrate solution (pH 8) of N-succinyl-DL-6-heptenylglycine was prepared by the same procedure as that in Example 5, and a cobalt chloride aqueous solution was added thereto to give a final concentration of 1 mM. To the resulting solution, a liquid culture of *E. coli* HB101 (pNIGHK), which was obtained by culture as in Example 6, was added (final substrate concentration: 9% by weight), and reacted at 45° C. As a result, 6-heptenylglycine was precipitated in the reaction mixture. The reaction mixture was stirred for 24 hours, and then the substrate and the product in the reaction mixture were analyzed by high performance liquid chromatography for the conversion (mol %). The conversion was 99.6 mol %. Then, the product was derivatized with di-tert-butyl dicarbonate to form N-tert-butoxycarbonyl-6-heptenylglycine, and the derivative was analyzed by high performance liquid chromatography for the optical purity (% e.e.). The optical purity was 100% e.e. The concentration of L-6-heptenylglycine accumulated, which was calculated from the conversion, was 5.7% by weight. Also, the dissolved concentration of L-6-heptenylglycine was determined by quantitative analysis using high performance liquid chromatography. The dissolved concentration was 0.5% by weight or lower.

<High Performance Liquid Chromatography Analysis Condition>
[Analysis of Conversion]
Column: YMC-A303 (4.6 mmφ×250 mm, produced by YMC Co., Ltd.)
Eluent: 20 mM phosphoric acid aqueous solution (pH 2.5)/acetonitrile=1/1
Flow rate: 1.0 ml/min.
Column temperature: 35° C.
Measuring wavelength: 210 nm
[Analysis of Optical Purity]
Column: CHIRALPAK AD-RH (4.6 mmφ×150 mm, produced by Daicel Chemical Industries, Ltd.)
Eluent: 0.02% phosphoric acid aqueous solution (pH 2.5)/acetonitrile=65/35
Flow rate: 0.7 ml/min.
Column temperature: 35° C.

The invention claimed is:

1. A method for producing an L-amino acid by hydrolyzing a succinyl group of an N-succinyl amino acid in an L-form selective manner with L-succinylase, while racemizing an enantiomeric mixture of the N-succinyl amino acid with N-acylamino acid racemase,
the reaction being performed with precipitating the produced L-amino acid.

2. The method according to claim 1,
wherein the L-amino acid has a dissolved concentration of 1% by weight or lower.

3. The method according to claim 1,
wherein the N-succinyl amino acid is represented by formula (I):

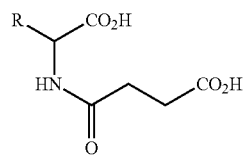

(I)

wherein R represents an optionally substituted C1 to C20 alkyl group, an optionally substituted C2 to C20 alkenyl group, an optionally substituted C2 to C20 alkynyl group, an optionally substituted C4 to C20 aryl group, or an optionally substituted C5 to C20 aralkyl group; and
the L-amino acid is represented by formula (II):

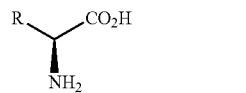

(II)

wherein R is the same as defined above.

4. The method according to claim 3,
wherein R in formula (I) and formula (II) is a 4-bromobenzyl group, a 3-fluorobenzyl group, a naothylmethyl group, an indanyl group, or a 6-heptenyl group.

5. The method according to any one of the claims 1 to 4,
wherein the enantiomeric mixture of the N-succinyl amino acid is racemized by a N-acylamino acid racemase obtained from a microorganism of the genus *Geobacillus* or *Thermus*, and the succinyl group of the N-succinyl amino acid is hydrolyzed by a L-succinylase obtained from a microorganism of the genus *Geobacillus*.

6. The method according to claim 5,
wherein the N-acylamino acid racemase is obtained from *Geobacillus kaustophilus* or *Thermus thermophilus*, and the L-succinylase is obtained from *Geobacillus kaustophilus*.

7. The method according to claim 6,
wherein the N-acylamino acid racemase is obtained from *Geobacillus kaustophilus* NBRC 102445 or *Thermus thermophiles* HB8, and the L-succinylase is obtained from *Geobacillus kaustophilus* NBRC 102445.

8. The method according to any one of claims 1 to 4,
wherein a transformant transformed by a vector that contains DNA encoding a N-acylamino acid racemase and DNA encoding a L-succinylase is used for hydrolyzing the succinyl group of the N-succinyl amino acid and racemizing the enantiomeric mixture of the N-succinyl amino acid.

* * * * *

SEQUENCE LISTING

<160> NUMBER OF SEQ ID NOS: 3

<210> SEQ ID NO 1
<211> LENGTH: 1170
<212> TYPE: DNA
<213> ORGANISM: Geobacillus kaustophilus

<400> SEQUENCE: 1

```
atgaaagaaa ttgttcagca gatgaaggcg gagctatggg agattttcga tcaccttcat      60
cgccatccag aaatcagttg ggaagagtgg caaacgaccg aatttcttcg gcgggagttg     120
gagcgcgaag ggtatcgggt gcggacgttt gccgattgtc cgggcgtggt ggcagaaatc     180
ggcgccggcc cgtttacggt cggggtgcgc agcgatatgg acgcccttg gcaagaagtg     240 aacggcgttt ggcagccgaa ccatgcgtgc gggcatgacg cccatatgac gatcgtgctc     300
ggggtggcga aactgcttcg ccgcatcggc tatgagccgc cggggacgct gcggtttttg     360
ttccagccgg ccgaggagaa aggaacaggg gcgttaaagc tgatcgaaaa aggggcggtt     420
gacggcgtgt cgttttata cggcattcat ctgcggccga ttcaagaagt gaaaggcgga     480
tatgcggcgc cggcgatcat ccatggggcg gcgcaatgca tcgaagggcg gattcgcggc     540
gtggcggcac atgccgcgcg gccgcattta ggcgtcaacg tcattgaagt cggcagcgcc     600
attgtccaag agctcggcaa aattcatatc gacccacaag tgccagcgtc gatcaaaatg     660
acgaagtttc acgccggtga aaaagatgcg aacacgatcc cggactacgc ggagtttgcc     720
cttgatttgc gggcgcaaac gaacgaggcg atggagcggc tcgtcgaggg gttgcgccat     780
```

```
gtgatcaacg gggtcgctgc gatttacgga gctgatattg agcttgttga gcggacgcgc    840
atcgtcgctg ctgatcctga tccagatgct gtgcggctga tggaggaggc gattatcacg    900
actttgggga cggaaaaatg cgttccgccg tcgtgacgt  cgggaggaga ggatttccat    960
ttttattcct ttaagaaacc ggagctgaaa acaacgatgc tcggattggg ctgcgacttg   1020
cgtccggggc tccatcaccc gaacatgacg ttccggcgcg atgatttgct ttctggcgtg   1080
gaaattttgg cgcgggttgt gatgaacaca tttgcgacgt ttgcgccgca ggggagaac    1140 gagcgtgcct ctgtcgctgc aaatcattga                                    1170

<210> SEQ ID NO 2
<211> LENGTH: 1128
<212> TYPE: DNA
<213> ORGANISM: Geobacillus kaustophilus

<400> SEQUENCE: 2
atggcgatca acatcgagta cgtcatattg cgccatttgc aaatggagtt gaaggcgccg     60
tttacaacga gctttggcac gtttcaaacg aaagagttta ttttagtgga agtcgtggat    120
tgcgacggcg tttccggctg gggcgaatcg gtcgcgtttt ccgtcccatg gtacagcgag    180
gaaacggtga aaacgaactg gcatatgctt gaagagtttc tcgtgccgct cttgttttcg    240
aagccgctta ggcatccagc ggaattgcca gagcgctttg ccgccatccg ccaaaacaac    300
atggcgaaag cggcgcttga gggagcggta tgggatttgt atgccaagcg gcttggcgtt    360
ccgctttgtc aagctctcgg gggaacgaaa aaggaaattg aagtcggcgt cagcatcggc    420
atccagccga cggtcgacga tctgcttcag gtgattgagc ggtatgtggc gcaagggtac    480
cggcggatca aagtgaagat caaaccggga tgggatgttg atgtcattcg cgacgtgcgg    540
cgcgcgtttc ctgacgtgcc gctcatggcg gatgccaatt cggcgtatac gctcgctgac    600
gccaagcggc ttcaggcgct tgatgaattt gggctgatga tgatcgaaca gccgctcgcc    660
gctgacgatc ttgtcgatca cgcccggctg cagccgcttc ttaagacgcc gatttgcctt    720
gatgaaagca ttcgttcata tgacgatgcg cgcaaggcgc ttgaccttgg cagctgccgc    780
atcatcaaca tcaaaatcgg gcgcgtcggc gggctttggg aggcgaagcg catccacgat    840 cttttgcgctg agcgaggcgt tccggtctgg tgcgggggga tgctggaagc aggggtcggg    900
cgcgcccaca atattgcgat cacgacgttg gaaaacttcg cgcttcccgg cgacaccgcc    960
gcgtcgtccc attattggga gcgggatatt atcacgccgg aagtcgaggt gcacaacggc   1020
ttgatccgcg tgccgaacgc cccgggcatc ggctatgacg tcgaccgccg ccaagttgag   1080
cggtatacgc agtttgccaa gttgttccat cgtacggcga cggcataa                1128

<210> SEQ ID NO 3
<211> LENGTH: 1110
<212> TYPE: DNA
<213> ORGANISM: Thermus thermophilus

<400> SEQUENCE: 3
atgcggatag aggcggccga gctcaggatt ttggagcttc ccctgaagtt ccgctttgag     60
acgagcttcg gggtgcagac caagaggacc atcctcctcc taaggctctt cggggagggc    120
ctggagggcc tggggggaagg ggtgatggag cgccttcccc tctaccggga ggagacggtg    180
gcgggggcca ggtacctcct ggaagaggtc ttcctgcccc gggtcctggg gcgggacctc    240
cccaaccccg aggccctaag ggaggccctt gccccttcc  ggggcaaccc catggccaag    300
gcggtcttgg agatggcctt ctttgacctc tgggccaagg ccctggggag gccgctttgg    360
```

```
caggtcctgg gcggggtgcg gcaggcggtg gaggtggggg tctccctggg gatccagccc      420
tcggtggagg acacgcttag ggttgtggag cggcacctcg aggagggcta ccgccgcatc      480
aagctcaaga tcaagccggg ctgggactac gaggtcctga aggcggtgcg agaggccttc      540
cccgaggcca ccctcaccgc cgacgccaac agcgcctata gcctcgccaa cctcgcccag      600
ctcaagcgcc tggacgagct ccggctggac tacatagagc agccctggc ctacgacgac       660 ctcctggacc acgccaagct ccagcgggag ctttccaccc ccatctgcct ggacgagagc      720
ctcacggggg cggagaaggc gaggaaggcc attgagcttg gggcgggccg ggtcttcaac      780
gtcaagcccg cccgcctcgg cggccacggg gagagcctcc gggtgcacgc cctggcggag      840
agcgccggga tccccctctg gatggggggg atgctggagg cgggggtggg gagggcccac      900
aacctccacc tggcgaccct tcccggcttc accaagcccg gggacgtgag ctcggcgagc      960
cgctactggg aggaggacat cgtggaggag gccctcgagg ccaaggacgg cctcatgccc     1020
gtgccggaag gcgtgggcat cggggtccac ctgaagcttc ccttcgtgga gcgggtcacg     1080
ctatggcaga ggtacatgtc cgcgagctaa                                      1110
```